(12) United States Patent
Hernley et al.

(10) Patent No.: US 11,719,675 B2
(45) Date of Patent: Aug. 8, 2023

(54) GAS DETECTION DEVICE FOR LITHIUM-ION BATTERY STORAGE SYSTEM

(71) Applicant: Battery Solutions, LLC, Wixom, MI (US)

(72) Inventors: Paul Andrew Hernley, Ann Arbor, MI (US); Donald Patrick Lynch, Howell, MI (US); Brian David Gregorka, Ann Arbor, MI (US); Thomas Bjarnemark, Howell, MI (US)

(73) Assignee: Battery Solutions, LLC, Wixom, MI (US)

( * ) Notice: Subject to any disclaimer, the term of this patent is extended or adjusted under 35 U.S.C. 154(b) by 1065 days.

(21) Appl. No.: 16/409,157

(22) Filed: May 10, 2019

(65) Prior Publication Data

US 2019/0348722 A1   Nov. 14, 2019

Related U.S. Application Data

(60) Provisional application No. 62/670,508, filed on May 11, 2018.

(51) Int. Cl.
*G01N 33/00* (2006.01)
*H01M 10/48* (2006.01)

(52) U.S. Cl.
CPC .......... *G01N 33/004* (2013.01); *H01M 10/48* (2013.01); *H01M 10/486* (2013.01); *H01M 10/488* (2013.01)

(58) Field of Classification Search
CPC ............ H01M 10/488; H01M 10/425; H01M 10/486; H01M 50/30; G01N 33/004; Y02E 60/10
See application file for complete search history.

(56) References Cited

U.S. PATENT DOCUMENTS

| | | | |
|---|---|---|---|
| 9,490,659 B1* | 11/2016 | English | H02J 7/35 |
| 10,877,011 B2* | 12/2020 | Cummings | G01N 27/04 |
| 2002/0120422 A1* | 8/2002 | Nagase | G05B 19/0423 |
| | | | 702/127 |
| 2011/0254559 A1* | 10/2011 | Nakashima | B60L 3/0046 |
| | | | 320/135 |
| 2014/0205867 A1* | 7/2014 | Hore | H01M 50/394 |
| | | | 429/50 |
| 2014/0269811 A1* | 9/2014 | Maleki | G01K 15/005 |
| | | | 374/1 |
| 2016/0049819 A1* | 2/2016 | Butler | H02J 7/342 |
| | | | 320/105 |
| 2017/0087963 A1* | 3/2017 | Tajima | B60H 3/06 |
| 2017/0331302 A1* | 11/2017 | Namiki | H01M 10/6235 |
| 2018/0003685 A1* | 1/2018 | Cummings | G01N 33/0063 |

(Continued)

*Primary Examiner* — Ojiako K Nwugo
(74) *Attorney, Agent, or Firm* — Brooks Kushman, P.C.

(57) ABSTRACT

A gas detection device for a drum containing lithium-ion batteries, may include a sensing component configured to be received by a threaded port of a lid of the container, the sensing component including at least one sensor configured to detect a gas concentration and a temperature of the drum, and a controller configured to receive the gas concentration and the temperature from the sensing component, and issue an alert in response to one of the gas concentration and the temperature exceeding an associated predefined threshold.

18 Claims, 3 Drawing Sheets

(56) References Cited

U.S. PATENT DOCUMENTS

| | | | | |
|---|---|---|---|---|
| 2018/0372054 A1* | 12/2018 | Chen | ........................ | H02J 7/345 |
| 2019/0101596 A1* | 4/2019 | Sakakibara | ......... | H01M 10/425 |
| 2019/0288327 A1* | 9/2019 | Yamashita | ............ | H01M 4/485 |
| 2019/0319466 A1* | 10/2019 | Pk | .......................... | G01K 13/00 |
| 2020/0106140 A1* | 4/2020 | Monismith | ......... | H01M 50/152 |

* cited by examiner

GAS DETECTION DEVICE FOR LITHIUM-ION BATTERY STORAGE SYSTEM

CROSS-REFERENCE TO RELATED APPLICATIONS

This application claims the benefit of U.S. provisional application Ser. No. 62/670,508 filed May 11, 2018, the disclosure of which is hereby incorporated in its entirety by reference herein.

TECHNICAL FIELD

Disclosed herein are gas detection devices for lithium-ion battery storage systems.

BACKGROUND

Lithium-ion batteries are often unstable and may generate a thermal event due to an internal or external short circuit, mechanical abuse, or exposure to high temperatures. A thermal event is the result of a phenomenon known as thermal runaway. A thermal runaway is the sudden increase in temperature and release of energy that may lead to a battery explosion, an example of a thermal event. Due to the increased use of lithium-ion batteries, mechanisms to safely store such batteries are in high demand.

SUMMARY

A gas detection device for a container containing lithium-ion batteries, may include a sensing component configured to be received by a threaded port of a lid of the container, the sensing component including at least one of a carbon monoxide or carbon dioxide sensor configured to sense an associated level carbon monoxide or carbon dioxide within the container; the sensing component further including a temperature sensor configured to detect a temperature within the container, and a controller configured to receive the associated level of carbon monoxide or carbon dioxide within the container and the temperature from the sensing component, and issue an alert in response to at one of the associated carbon monoxide level or associated carbon dioxide level or the temperature exceeding an associated predefined threshold.

A gas detection device for a drum containing lithium-ion batteries, may include a sensing component configured to be received by a threaded port of a lid of the container, the sensing component including at least one sensor configured to detect a gas concentration and a temperature of the drum, and a controller configured to receive the gas concentration and the temperature from the sensing component, and issue an alert in response to one of the gas concentration and the temperature exceeding an associated predefined threshold.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

A lithium-ion battery is often placed in a storage container as an end-of-life procedure before battery disposal or recycling. A single lithium-ion battery with one anode and one cathode is referred to as a cell and a battery module is formed from connecting multiple cells in either series or parallel. A battery pack is formed from connecting multiple modules, also in either series or parallel. Any combination of cells, modules, or packs may be stored in one storage container. A thermal event such as thermal runaway begins at a cell level when an increase in temperature of a cell causes a further increase in temperature. In the case where multiple cells are disposed closely next to each other, heat and energy released from one cell will cause a thermal event at a neighboring cell and thermal runaway will keep moving cell to cell through the module or the pack. Lithium-ion batteries release carbon monoxide (CO) and carbon dioxide ($CO_2$) during an initial stage of a thermal event. Gas detection devices that sense CO and $CO_2$ installed in a storage container lid may identify a thermal event in a single lithium-ion cell before the thermal event spreads to neighboring lithium-ion cells.

Disclosed herein is a gas detection device for bulk storage of lithium-ion batteries. The gas detection device is to be used for storing used lithium ion batteries at an end-of-life condition when a cell is particularly susceptible to a thermal event. The disclosed gas detection device may be suitable in any situation which requires storage of lithium-ion batteries before disposal or recycling.

A typical lithium-ion battery storage container is often a metallic drum with an inner non-conductive lining. The metallic drum has a lid with at least one threaded port. Here, the gas detection device is disposed in the port on the drum lid. The gas detection device can measure CO and $CO_2$ concentrations inside the metallic drum at levels low enough to detect a thermal event of a single 18650 cell disposed within the otherwise empty drum. The gas detection device may measure baseline CO and $CO_2$ concentrations within the drum and also measure an increase in CO and $CO_2$ concentrations over time within the drum to detect a first occurrence of a thermal event of a single cell.

Figure 1A:
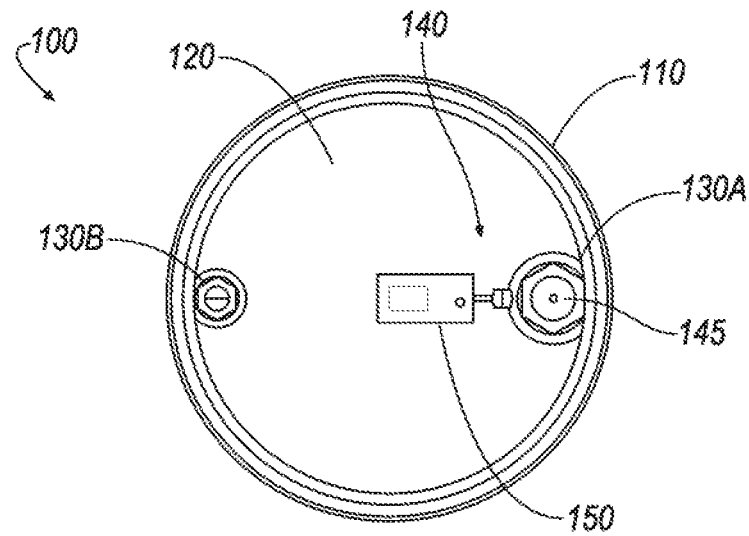
FIG. 1A illustrates a front view of an example battery storage container having a gas detection device.
Figure 1B:
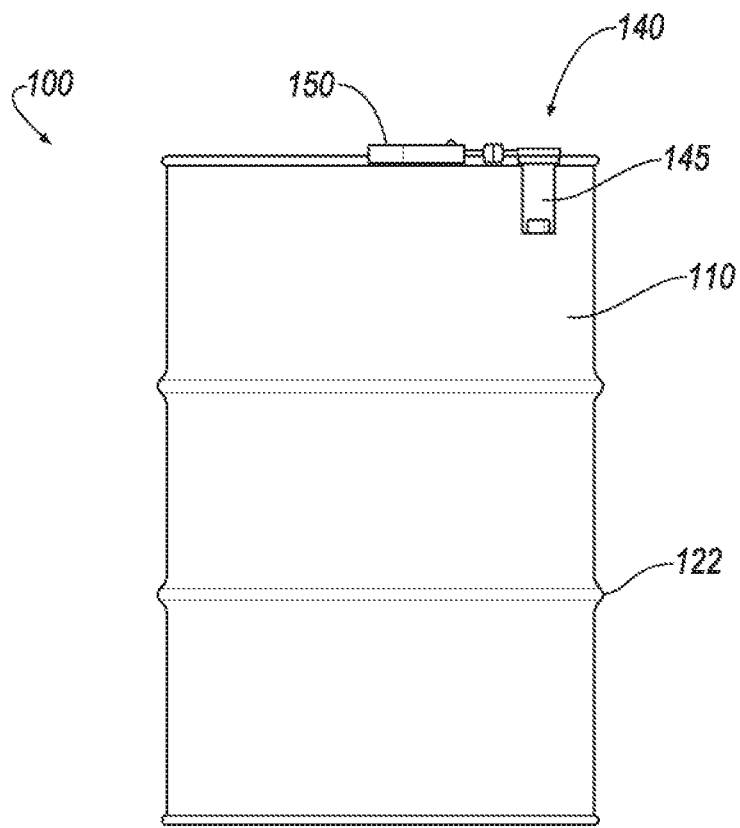
FIG. 1B illustrates a side view of the example battery storage container of FIG. 1A.

FIGS. 1A and 1B illustrate an example lithium-ion battery storage system 100 having at least one battery storage container 110. The storage container 110 may be a case, a barrel, or a drum such as a 55-gallon drum typically configured to store solid and liquid items. The container 110 (also referred to herein as drum 110) may be metallic with a non-conductive liner, plastic, laminated paperboard, or may be formed from a fireproof or fire-resistant material. The storage container 110 may have layers of heat dissipation insulation. The storage container 110 may have one or more reinforcement rings 122 formed around a perimeter of the container and formed from a same material as the container to increase structural rigidity of the container.

The storage container 110 may be hermetically sealed via a lid 120. As explained above, the container 110 may be configured to store lithium-ion batteries therein. The storage container 110 and the lid 120 may form an air-tight seal with a gasket (not labeled in FIGS. 1A and 1B). The seal may be formed by a mechanical ring clamp or a lever lock ring clamp. The mechanical ring clamp or lever lock ring clamp may be disposed around a perimeter of a top of the storage container 110 and a perimeter of the lid 120 and may apply torque to seal the container 110 to the lid 120.

The lid 120 may define at least one threaded port 130A, 130B (collectively referred to as thread ports 130). The threaded port 130 may be an opening or a bung hole in the lid to receive a bung, plug, or other device. In one example, the lid 120 has two threaded ports, individually labeled as a first thread port 130A and a second thread port 130B. The threaded ports 130 may vary in size from ¾-inch diameter to 2-inch diameter. In one example, the first thread port 130A may have a 2-inch diameter, while the second thread port 130B may have a ¾-inch diameter.

A gas detection device 140 may be partially installed through the threaded port 130. In one example, a National Pipe Thread Taper (NPT) is used with the threaded port 130 and the gas detection device 140 to form a fluid-tight and gas-tight seal.

The gas detection device 140 may include a sensing component 145 and a communication component 150. The sensing component 145 of the device 140 may be arranged within, or partially within the drum 110 and may be inserted into the first port 130A. During installation, the sensing component 145 may be screwed into the drum 110 so that a CO/CO2 sensor and pressure/temperature probes of the sensing component 145 are inside the drum. The sensor and P/T probes may be easily replaceable. The sensing component 145 may be configurable to detect different gasses. The sensing component 145 may be configured to detect the gas concentration and temperature within the sealed drum.

The communication component 150 may be arranged on the exterior of the drum on the lid 120. When in an installed state, the gas detection device 140 may be approximately 3-6 inches tall off of the lid 120, or as little as 1 inch tall off of the lid 120. During storage and transportation, a 33.5 inch drum may be placed on a 6.5 inch tall pallet (or more or less) and loaded into a rack that has a 52 inch vertical beam to beam space. A minimum of 6 inches may be preserved between the top of the drum 110 and the bottom of the rack beam above it. Thus, approximately 7.5 inches of space is available on top of the drum lid 120 in this specific example.

Each of the sensing component 145 and the communication component 150 may include a housing made of Acrylonitrile Butadiene Styrene (ABS) or appropriate thermal plastic material.

Figure 2A:
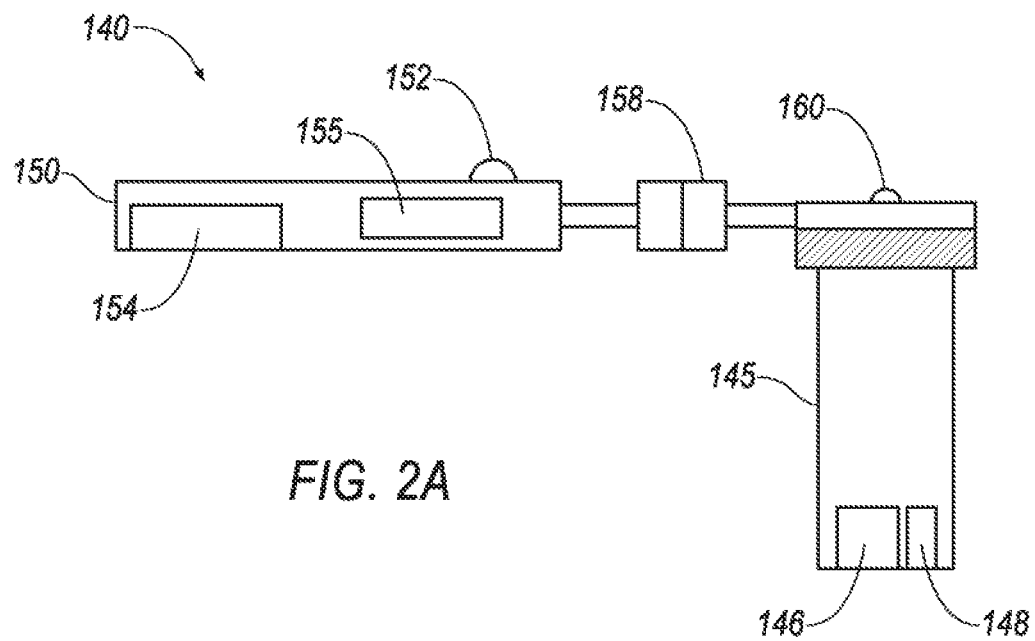
FIG. 2A illustrates a side view of an example of a detailed view of a gas detection device.
Figure 2B:
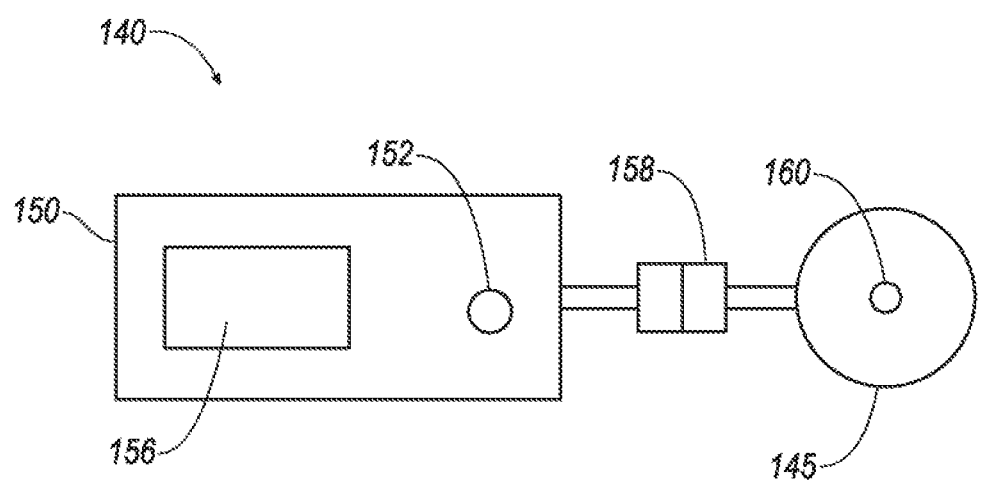
FIG. 2B illustrates a top view of the gas detection device of FIG. 2A.

FIGS. 2A and 2B illustrate an example of a detailed view of the gas detection device 140. The gas detection device 140 has a sensing component 145 and a communication component 150. The sensing component 145 may include at least one sensor. For example, the sensing component 145 may include a CO/$CO_2$ sensor 146 and a temperature sensor 148.

The CO/$CO_2$ sensor 146 may be a CO—carbon monoxide, a $CO_2$—carbon dioxide, or a combined CO and $CO_2$ sensor. In one example, the sensor 146 is configurable to sense either or both CO and $CO_2$ within the drum 110 storing used lithium-ion batteries. The sensor 146 may be capable of accurately measuring CO concentration from <1 ppm to 1000 ppm and/or $CO_2$ concentration from 300 ppm to 5000 ppm.

The temperature sensor 148 may be a sensor configured to detect pressure and/or temperature of the interior of the drum 110. The temperature sensor 148 may be able to measure temperature from roughly 32° F. to 500° F.

The sensing component 145 may transmit the sensor data to a processor 155 of the communication component 150 periodically, e.g., at predefined increments such as every 5 seconds to every 5 minutes. The sensor data may include the gas concentration, temperature, location and timestamp.

The communication component 150 may include the processor 155 (or controller) configured to receive and transmit data among the various components of the device 140. For example, the communication component 150 may be configured to receive sensor data from the sensing component 145, and issue alerts based on that data. The communication component 150 may include an indicator light 152, a power source 154, a display 156, and an interface 158 to connect one communication module 150 to a neighboring communication module.

The power source 154 may be a disposable battery, a rechargeable battery, or an AC power supply. The power source may provide electric power to the device 140.

The processor 155 may be a controller such as a stand-alone device that include a combination of both hardware and software components and may be configured to analyze and process data provided by the sensing component 145. Specifically, the controller may be configured to indicate a drum status based on the sensor data.

The indicator light 152 may be arranged on a top of the communication component 150. The indicator light 152 may include a single light, such as a light emitting diode (LED). The indicator light 152 may be configured to alternate between various colors and states based on the sensor data. The processor 155 may instruct the indicator light 152 to illuminate based on the received sensor data. For example, each color and state may indicate a specific mode of the gas detection device 140. For example, a flashing green light may indicate a normal mode, a flashing yellow light may indicate an at-risk mode. A flashing red light may indicate an immediate risk mode. A solid yellow light may indicate an error mode. A solid green light may indicate a low battery mode. Such modes may be based on the level of carbon monoxide or carbon dioxide, or the temperature.

These modes may be determined by the sensor data provided to the processor 155 by the sensing component 145. For example, certain temperature thresholds and ranges may be set to trigger certain modes and conditions. A temperature between 90 and 100° F. may result in the drum state being in an at-risk mode. A temperature over 100° F. may result in the drum state being in an immediate risk mode.

Certain CO and $CO_2$ readings may also trigger certain modes for certain ppm values. For example, $CO_2$ levels between 700 and 1000 ppm may indicate an at-risk mode. $CO_2$ levels above 1000 ppm may indicate an immediate risk mode. CO levels between 10 and 50 ppm may indicate an at-risk mode. CO levels between 50 and 100 ppm may indicate an immediate risk mode. Thus, CO levels over 50 ppm and $CO_2$ levels above 1000 ppm may exceed the predefined threshold for immediate risk. Such immediate risk may result in the processor 155 issuing an alert by instructing the indicator light 152 to adjust its color to red, or flashing red.

The display 156 may be a visual display configured to provide information to a user. The display may be a light-emitting diode display (LED), Electroluminescent display (ELD), Electronic paper, E Ink, Plasma display panel (PDP), Liquid crystal display (LCD), Organic light-emitting diode display (OLED), etc. the display may present data similar to the sensor data such as the ppm, temperature, pressure, time of alarm start, time on battery/charge remaining, error codes, etc. The display may also display certain instructions or alerts, such as "remove this drum" in response to the sensor data. The display may indicate the mode, such as "immediate mode" or "at-risk mode."

The interface 158 may be a communication bus configured to transmit data between the sensing component 145 and the communication component 150.

The gas detection device 140 may also have a pressure release valve 160. The pressure release valve 160 may vent gas pressure to outside of the drum 110 if the gas pressure within the drum 110 exceeds a predetermined pressure limit. This may prevent pressure as a certain PSI to prevent explosion and allow building smoke detectors to function properly.

A data collection unit may collect data from the sensor 146 in periodic increments to determine a baseline gas concentration level within the drum. The data collection unit may continue to collect data from the sensor 146 in periodic increments and send this data to a control unit via a wireless communication signal. The wireless communication signal may be a Bluetooth® connection or a WiFi® connection. The control unit may be a computer, a tablet, a phone, or a web-based app. The indicator light 152 may have a color scheme corresponding to different status conditions within the drum 110. In one example, the indicator light may change color if the gas concentration within the drum 110 exceeds a predetermined gas concentration limit.

Figure 3:
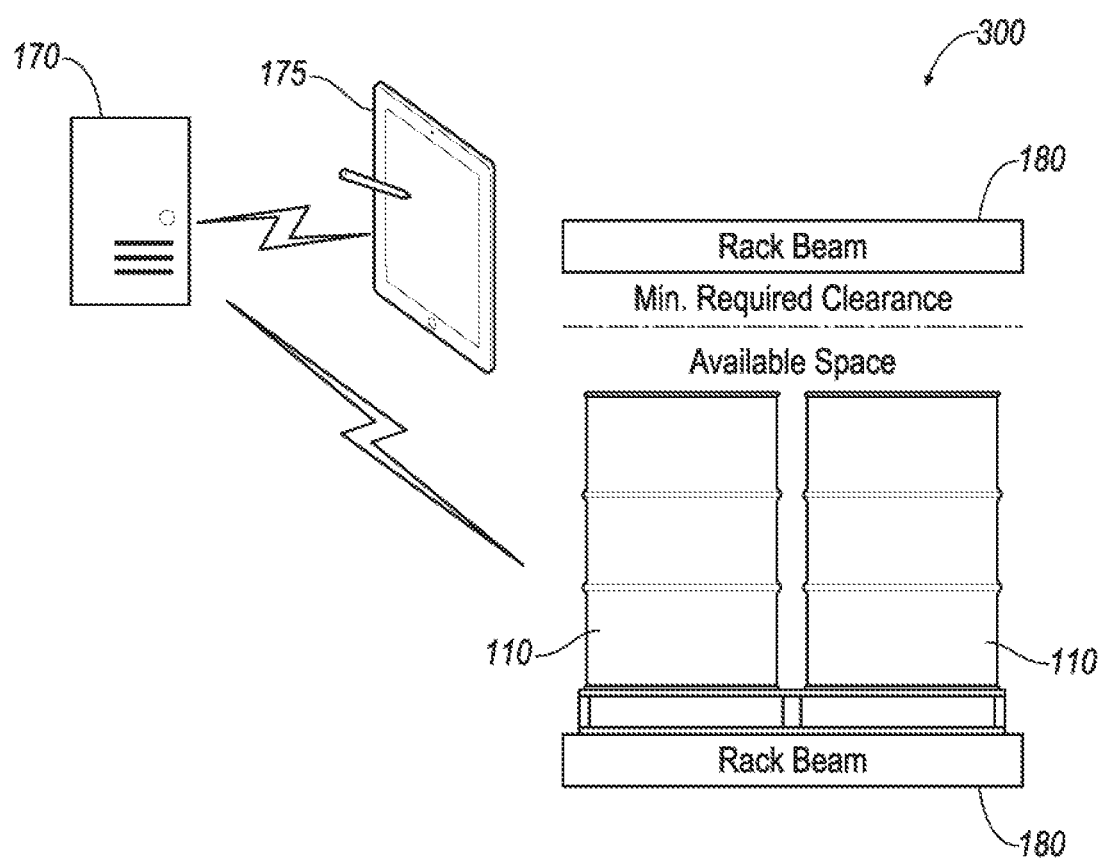
FIG. 3 illustrates an example of a battery storage container installed in a warehouse.

FIG. 3 illustrates an example of a battery storage system 300. The battery storage system 300 may include a plurality of drums 110 arranged on a rack beam 180. The rack beam 180 may be stored within a warehouse used to store lithium-ion batteries at the end-of-life condition. The battery storage drum 110 may be stored on the rack beam 180 next to an adjacent battery storage drum 110. The gas detection device 140 (not shown in FIG. 3) installed on the lid 120 may add three inches or less of height to the drum. Multiple rack beams 180 and battery drums 110 are stored in one warehouse.

The communication component 150 of the gas detection device 140 may include a wireless transceiver (not shown) configured to communicate wirelessly with various other components and devices. For example, the gas detection device 140 may communicate with a remote server 170. The remote server 170 may be arranged within the warehouse remote from the rack beams 180, or at another location or building. The remote server 170 may communicate with a computing device 175. The computing device 175 may include a display configured to display information about the storage system 300. The computing device 175 may be a personal computer, tablet computer, cellular phone, etc. The computing device 175 may facilitate remote monitoring of the system 300 and each of the gas detection device 140. The display may be configured to show pallet locations on a map of the facility, as well as the drum mode for each of the drums. The computing device 175 and/or remote server 170 may allow for set point of the alarms to be adjusted for each device independently, as well as allow for calibration of the devices 140. The computing device 175 may facilitate control of the system 300 and associated devices 140 via a web-based interface.

Accordingly, disclosed herein is a reaction detection system for lithium-ion battery storage. As explained above, lithium-ion batteries are ubiquitous in everyday life, and over the next decade we expect to see considerable growth in this market. These particular batteries are unstable and have been involved in numerous thermal events that are generally caused by short circuits or mechanical/thermal abuse. Batteries are currently stored in 55-gallon steel drums that are lined with a plastic film. Our safety goal is to identify the first occurrence of a thermal runaway event in these drums so that we can remove them from our facility before the event becomes unmanageable.

Recent work has shown that lithium-ion batteries release CO and CO2 (carbon monoxide and carbon dioxide) during the early stages of a thermal event. On a worst-case basis, we expect a single 18650 cell in an otherwise empty 55-gallon drum to increase the CO and CO2 concentrations by about 30 ppm and 540 ppm, respectively. The baseline CO and CO2 concentrations in normal air should be <5 ppm and 400-450 ppm, respectively. This worst-case scenario is significant enough to provide an easily noticeable change in the composition of the air inside the drum with existing gas sensor technology.

Since the gases released from a single 18650 cell are detectable inside a 55-gallon drum, gas detection can identify the first occurrence of a thermal event before it spreads to neighboring lithium-ion cells. This is key to keeping facilities safe.

Pressure and temperature sensors may be used to supplement gas detection. In an enclosed drum that is air-tight, it is reasonable to expect around a 2% internal pressure increase during the release of gases from the first cell to vent. These gases may be warmer than the ambient temperature. These spikes in pressure and temperature may also be useful for detecting the first thermal event.

The gas detection device may measure the concentration of CO and/or CO2 and the temperature and pressure inside a 55-gal drum. It should screw into the 2% NPT port on the lid. It may be battery-powered and have a run-time greater than 1 year. The device may connect to a control station (desktop computer) or a web-based app so it can be monitored on-site and also through the internet. The device may be disposed of upon depletion of the battery but would need to be sufficiently cost-effective to do so.

The embodiments of the present disclosure generally provide for a plurality of circuits, electrical devices, and at least one controller. All references to the circuits, the at least one controller, and other electrical devices and the functionality provided by each, are not intended to be limited to encompassing only what is illustrated and described herein. While particular labels may be assigned to the various circuit(s), controller(s) and other electrical devices disclosed, such labels are not intended to limit the scope of operation for the various circuit(s), controller(s) and other electrical devices. Such circuit(s), controller(s) and other electrical devices may be combined with each other and/or separated in any manner based on the particular type of electrical implementation that is desired.

It is recognized that any controller as disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any controller as disclosed utilizes any one or more microprocessors to execute a computer-program that is embodied in a non-transitory computer readable medium that is programmed to perform any number of the functions as disclosed. Further, any controller as provided herein includes a housing and the various number of microprocessors, integrated circuits, and memory devices ((e.g., FLASH, random access memory (RAM), read only memory (ROM), electrically programmable read only memory (EPROM), electrically erasable programmable read only memory (EEPROM)) positioned within the housing. The controller(s) as disclosed also include hardware based inputs and outputs for receiving and transmitting data, respectively from and to other hardware based devices as discussed herein.

With regard to the processes, systems, methods, heuristics, etc., described herein, it should be understood that, although the steps of such processes, etc., have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A gas detection device for a container containing lithium-ion batteries, comprising: a sensing component configured to be received by a threaded port of a lid of the container, the sensing component configured to sense at least one of a carbon monoxide level, a carbon dioxide level, or temperature within the container; at least one indicator light; and a controller configured to receive the at least one of the carbon monoxide level, the carbon dioxide level, or the temperature from the sensing component, and adjust the color of the indicator light based on a mode defined by at least one of the of carbon monoxide level, carbon dioxide level, or the temperature exceeding an associated predefined threshold.

2. The device of claim 1, wherein the controller is further configured to identify an immediate mode in response to at least one of the temperature exceeding 100 degrees Fahrenheit, the carbon monoxide level exceeding 50 ppm, or the carbon dioxide level exceeding 1000 ppm.

3. The device of claim 1, wherein the controller is further configured to identify an at-risk mode in response to at least one of the temperature exceeding 90 degrees Fahrenheit, the carbon monoxide level exceeding 700 ppm, or the carbon dioxide level exceeding 50 ppm.

4. The device of claim 1, further comprising at least one display configured to display the at least one of the carbon monoxide level, the carbon dioxide level, or the temperature.

5. The device of claim 1, further comprising a pressure release valve configured to vent gas pressure within the container.

6. A gas detection device, comprising:
a sensing component configured to be received by a threaded port of a lid of a drum including lithium-ion batteries,
the sensing component including at least one sensor configured to detect a gas concentration and a temperature of the drum,
at least one display configured to display at least one of the gas concentration or the temperature, and
a controller configured to receive the gas concentration and the temperature from the sensing component, and issue an alert in response to one of the gas concentration or the temperature exceeding an associated predefined threshold.

7. The device of claim 6, further comprising at least one indicator light configured to change color in response to at least one of the gas concentration and the temperature exceeding the associated predefined threshold.

8. The device of claim 7, wherein the controller is further configured to adjust the color of the at least one indicator light in response to the gas concentration and the temperature each being within an associated predefined range.

9. The device of claim 6, wherein the gas concentration includes at least one of a carbon monoxide level or a carbon dioxide level.

10. The device of claim 9, wherein the controller is configured to identify an immediate mode in response to at least one of the temperature exceeding 100 degrees Fahrenheit, the carbon monoxide level exceeding 50 ppm, or the carbon dioxide level exceeding 1000 ppm.

11. The device of claim 9, wherein the controller is configured to identify an at-risk mode in response to at least one of the temperature exceeding 90 degrees Fahrenheit, the carbon monoxide level exceeding 700 ppm, or the carbon dioxide level exceeding 50 ppm.

12. The device of claim 6, further comprising a pressure release valve configured to vent gas pressure within the drum.

13. The device of claim 6, wherein the sensing component does not extend beyond three inches on the lid.

14. The device of claim 6, further comprising a housing configured to maintain the controller, the housing being composed of a thermal plastic material.

15. The device of claim 6, wherein the sensing component is configured to transmit the gas concentration or the temperature to the controller at predefined increments.

16. The device of claim 6, wherein the sensing component is configured to transmit, the controller, a signal identifying a location of the drum and timestamp data indicative of a time the sensing component acquired the at least one gas concentration and temperature.

17. The device of claim 6, further comprising a power source configured to provide electric power to the sensing component and controller.

18. A gas detection device, comprising:
a sensing component configured to be received by a threaded port of a lid of a drum including lithium-ion batteries,
the sensing component including at least one sensor configured to detect at least one of a gas concentration and a temperature of the drum, wherein the sensing component does not extend beyond three inches on the lid, and a controller configured to receive the gas concentration and the temperature from the sensing component, and issue an alert in response to one of the gas concentration or the temperature exceeding an associated predefined threshold.

* * * * *